Figure 8:
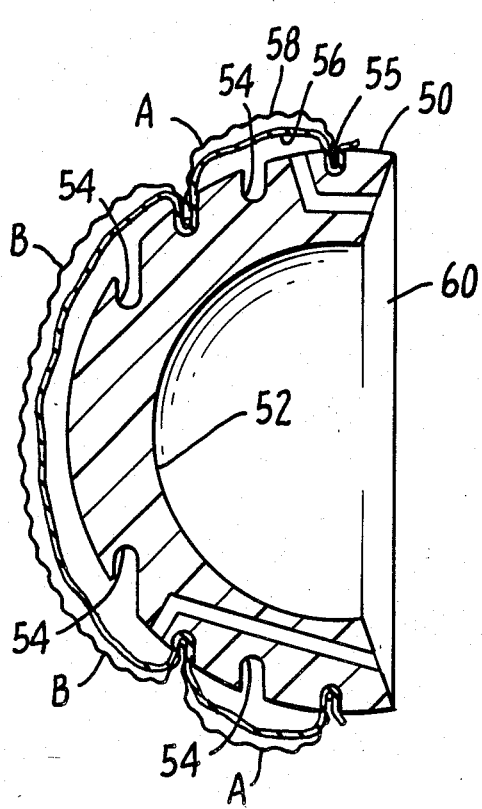

United States Patent [19]

Powlan

[11] Patent Number: 4,888,024
[45] Date of Patent: Dec. 19, 1989

[54] PROSTHETIC DEVICE AND METHOD OF FIXATION WITHIN THE MEDULLARY CAVITY OF BONES

[76] Inventor: Roy Y. Powlan, 1 Chapel Dr., Lafayette, Calif. 94549

[21] Appl. No.: 28,104

[22] Filed: Mar. 19, 1987

Related U.S. Application Data

[63] Continuation-in-part of Ser. No. 769,309, Nov. 8, 1985, abandoned.

[51] Int. Cl.$^4$ .......................... A61F 2/36; A61F 2/34; A61F 2/32
[52] U.S. Cl. .......................................... 623/23; 623/22; 623/16
[58] Field of Search .............................. 623/22, 23, 16; 128/92 R

[56] References Cited

U.S. PATENT DOCUMENTS

| | | | |
|---|---|---|---|
| 3,924,274 | 12/1975 | Heinke et al. | 623/23 X |
| 4,064,567 | 12/1977 | Buestein et al. | 623/23 X |
| 4,357,716 | 11/1982 | Brown | 623/23 |
| 4,399,814 | 8/1982 | Pratt, Jr. et al. | 128/92 R X |
| 4,488,549 | 12/1984 | Lee et al. | 623/16 X |
| 4,562,598 | 1/1986 | Kranz | 623/22 X |
| 4,593,685 | 6/1986 | McKay et al. | 128/92 R X |
| 4,619,659 | 10/1986 | Witzel | 623/23 |

Primary Examiner—Richard J. Apley
Assistant Examiner—Alan W. Cannon
Attorney, Agent, or Firm—John R. Murtha

[57] ABSTRACT

A prosthesis, adapted for fixation within the medullary cavity of a human bone, having an orthopedic device to which a nonresorbable, flexible membrane is attached in a liquid and air-tight manner. A flexible woven sheath encompasses the membrane and the prosthesis is provided with means for introducing liquid cement under pressure internally of the membrane to force the membrane and sheath outwardly into firm engagement with the walls of the bony cavity to fix the prosthesis in the cavity once the cement has hardened. The membrane prevents any chemical interaction between the cement and bodily fluids.

18 Claims, 3 Drawing Sheets

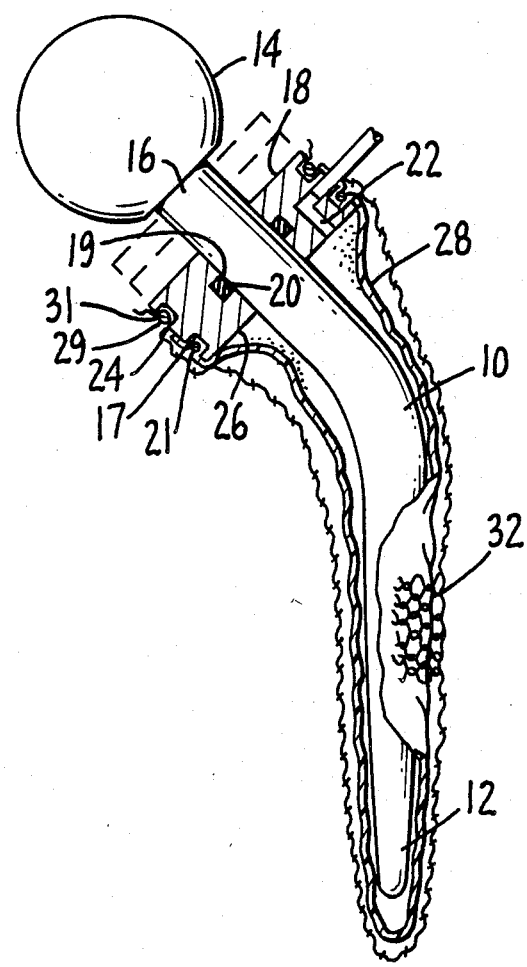
FIG._1.
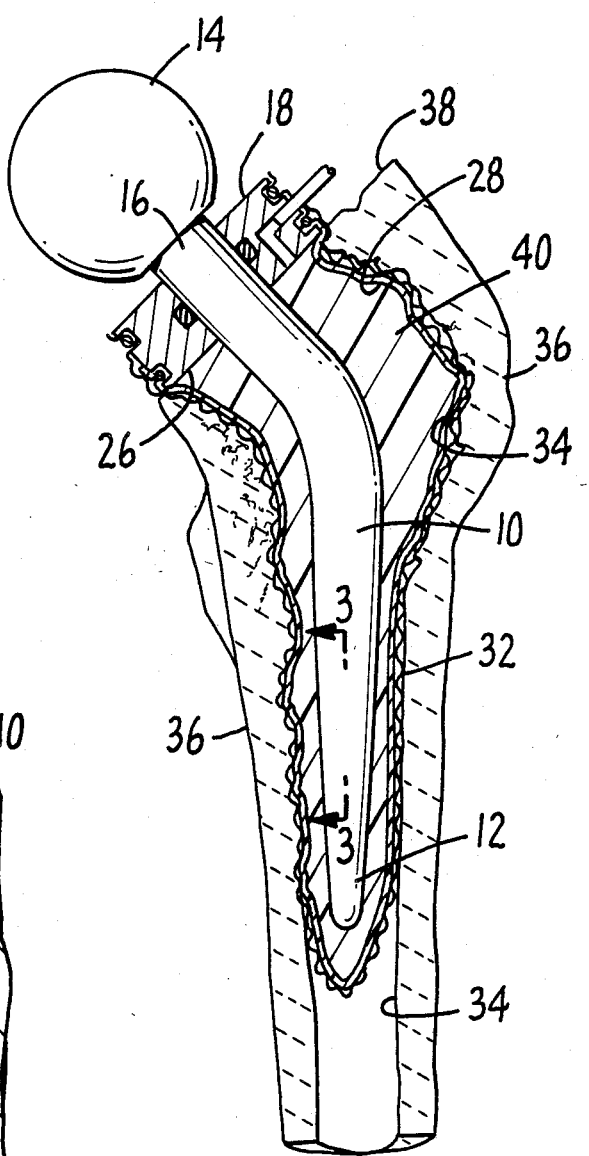
FIG._2.
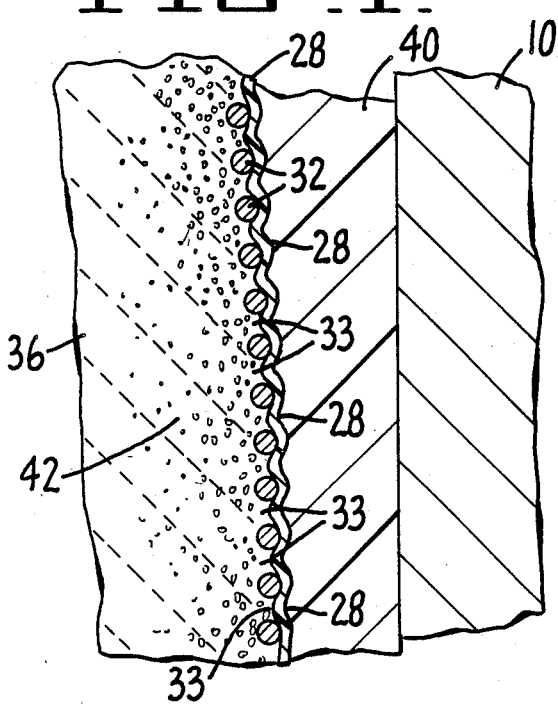
FIG._3.

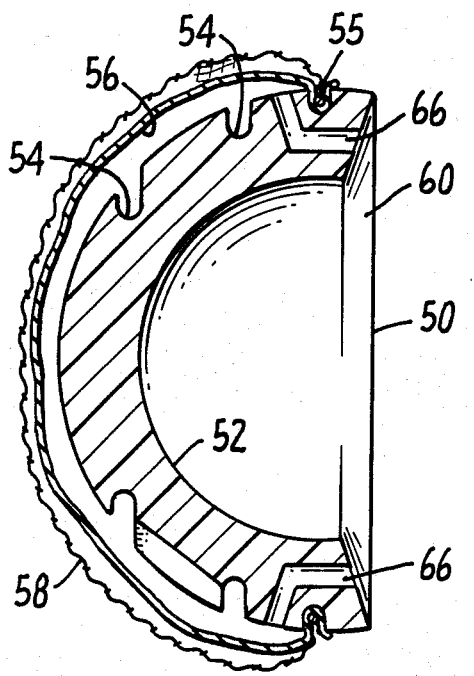
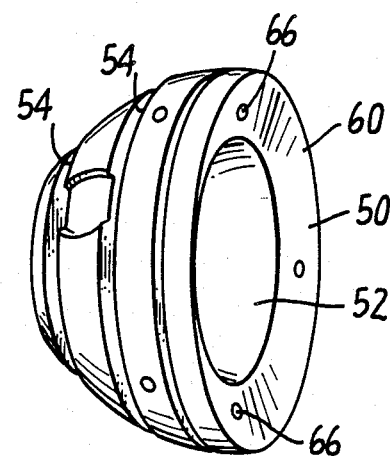
FIG. 5.
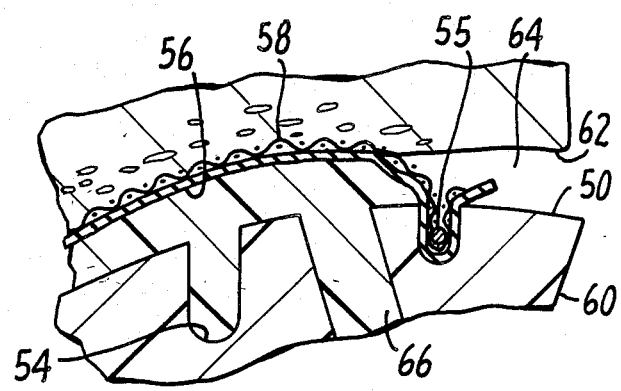
FIG. 7.
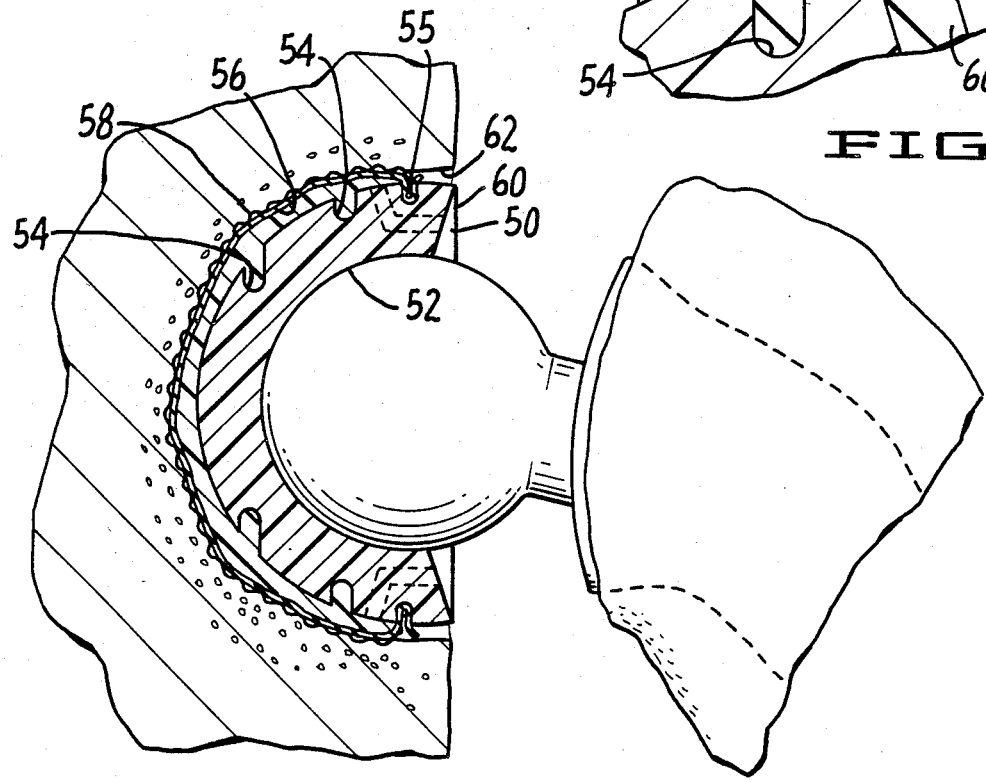
FIG. 4.
FIG. 6.

PROSTHETIC DEVICE AND METHOD OF FIXATION WITHIN THE MEDULARY CAVITY OF BONES

This application is a continuation-in-part application of my pending application Ser. No. 06/796,309, filed Nov. 8, 1985, abandoned June 5, 1987.

The invention relates to prosthetic devices and to a method of fixation of such devices within the medullary cavity of bones. While the device is especially adapted for the fixation of a prosthetic device in the proximal end of the femoral bone during a total hip replacement, the device can be used to fix orthopedic components within the medullary cavity of bones at other sites in the body such as the distal end of the femur and the proximal end of the tibia as part of total knee surgery, or, for that matter, in any other portion of the body in which an orthopedic device is to be fixed within a bone cavity.

Currently, one method of fixation of a femoral prosthesis into the proximal femur utilizes a bone cement which serves as a grouting that holds the prosthesis in the medullary cavity once it has hardened. This method has been found to have certain disadvantages. The most often used cement, methylmethracrylate, has been found to react with tissue fluids when in contact with living bone with the result that the bond between the cement and the bone is weakened. Additionally, the cement tends to become brittle with age and exposure to tissue fluids and the cumulative effect of these problems frequently leads to a failure of the bond after several years and a loosening of the prosthesis. Replacement of the loosened prosthesis is difficult since the cement must be broken up and removed from the medullary cavity. This requires chiseling into and reaming down the bony cavity with the risk of fracturing or perforating the bone.

To circumvent these problems efforts have been made to effect a cementless, mechanical fixation of the femoral component in the medullary canal. In one method the femoral cavity is chiseled to a configuration that closely fits the shape of the metal component inserted into it so as to produce a very tight mechanical fit between the prosthesis and the bone cavity. In modifications of this method, the outer surface of the prosthesis has been provided with fine wires or beads to encourage the patient's bone to grow into the interstices of this surface treatment and add additional fixation of the component in the cavity. Unfortunately, these efforts have not been very successful because the wide variations from patient to patient in the size, shape and quality of bone make it exceedingly difficult to achieve a perfect mechanical fixation of the prosthesis in the femoral bone.

The object of the present invention is to provide an improved prosthetic device that will not be subject to the drawbacks of the prior art and to also provide an improved method of fixing the prosthetic device within the medullary cavity of a bone.

Figure 9:
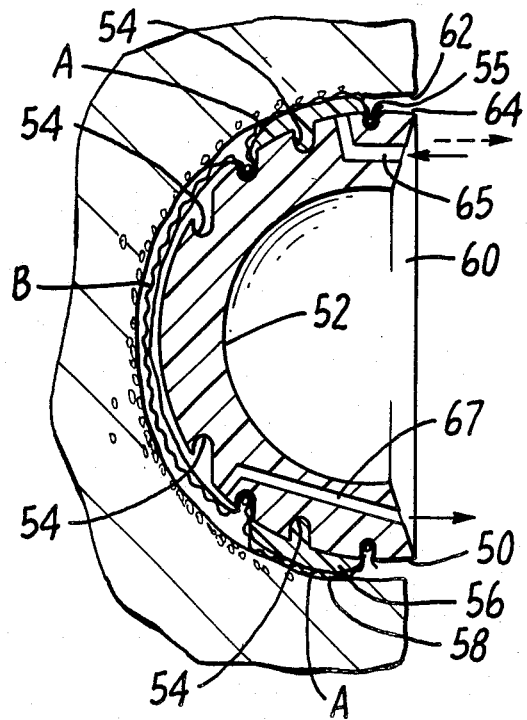
Figure 11:
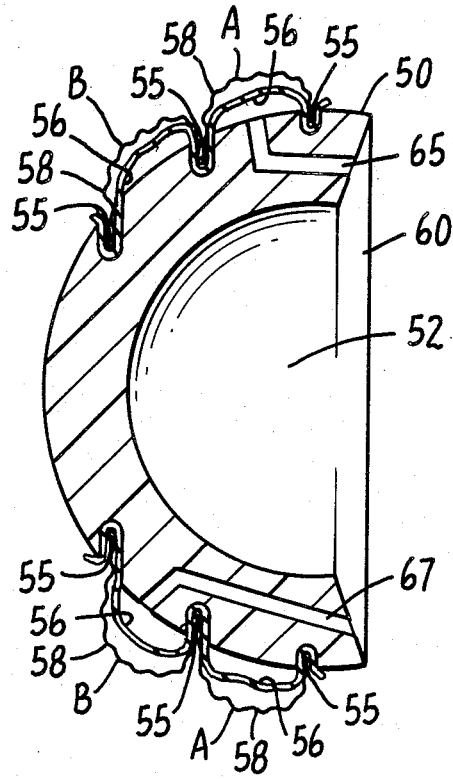
Figure 10:
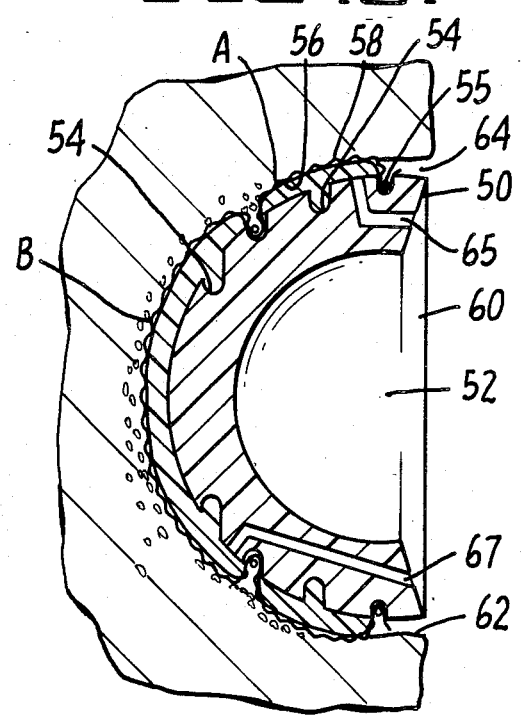

A preferred embodiment of the invention is shown in the accompanying drawings in which similar reference numerals refer to similar parts, FIG. 1 is a side elevational view, partly in section, showing a preferred embodiment of the invention, FIG. 2 is another side elevational view, partly in section, showing the manner in which the prosthetic device of the invention is fixed within the medullary cavity of the patient's femoral bone, FIG. 3 is a partial, sectional view showing how the applicant's prosthetic device interfaces with the living bone of the patient, FIG. 4 is a sectional view of an alternate form of the invention adapted for insertion into a patient's acetabular cavity, FIG. 5 is a perspective view of an acetabular cup as modified in accord with the teachings of applicant's invention, FIG. 6 is a side view, partly in section, showing the fixation of an acetabular cup into the acetabular cavity of a patient together with the femoral element of a total hip replacement, FIG. 7 is a partial, sectional view showing how the applicant's prosthetic device interfaces with the patient's acetabular cavity, FIG. 8 is a sectional view showing a still further modification of the applicant's invention in which the membrane and sheath are formed into two separate chambers, FIG. 9 is a sectional view showing the initial phase of the fixation of the prosthesis of FIG. 8 to the acetabular cavity of a patient, FIG. 10 is a sectional view showing the complete fixation of the modification of FIG. 8 to the acetabular cavity of a patient, and FIG. 11 is a sectional view of a still further modification of the invention.

As is best seen in FIG. 1, the applicant's improved prosthesis comprises a solid metal arbor 10, which in this instance, is curved so as to generally conform to the medullary cavity in the proximal end of the patient's femoral bone. In addition to being curved, the metal arbor 10 also tapers toward its distal end 12 inasmuch as the medullary canal within the femur narrows as it approaches the midportion of the bone. Fixedly mounted on the outer end of the arbor 10 is a femoral ball head 14 that is designed to pivotally seat within a hemispherical cavity in an acetabular element (not shown) fixed in the patient's acetabulum.

The upper portion 16 of the arbor 10 comprises a straight section of uniform diameter and has an annular split collar 18 mounted thereon. The respective halves of the split collar 18 are secured together through the use of screws (not shown) or other suitable fastening means. As indicated in FIG. 1, the collar 18 may be selectively positioned at different points along this upper portion 16 of the arbor 10 so as to serve as a locating means for the arbor for reasons that will be described later. A liquid and air tight seal is made between the collar 18 and the arbor 10. To this end an O ring 20 is first inserted over the lower, or distal, end 12 of the arbor and then positioned on the upper portion 16. An internal groove 19 is formed in each half of the split collar 18 and receives the O ring once the collar has been positioned on the arbor 10. The collar 18 is also provided with an internal passageway 22 that communicates the outer periphery 24 of the collar with its lower, or inner, face 26.

A thin, flexible, open-ended, balloon-like membrane 28 is secured to the collar 18 in any suitable manner that provides an air and liquid tight seal between the collar and the membrane. In the form of the invention shown in the drawings, the collar 18 has a circumferential groove 17 formed in its outer periphery 24 and a lock ring 21 secures the outer edge of the membrane therein. The membrane 28 passes down and around the distal end 12 of the arbor 10 so as to completely encompass it.

The membrane 28 may be made of any suitable material that is flexible and impervious and nonreactive to bodily fluids. The phrase "nonreactive to bodily fluids" means that the membrane will not be absorbed by the body over a period of time and, thus, constitutes a nonresorbable membrane. A preferred material that possesses these properties is polyurethane film. In addition to the membrane 28, a thin, flexible open-ended sheath 32 of tightly woven metallic threads is also secured to the collar 18. A second circumferential groove 29 is formed in the periphery 24 of the collar just above the circumferential groove 17. A lock ring 31 fixedly secures the outer edge of the metallic sheath 32 in the groove 29. The sheath 32 lies outside the membrane 28 and encompasses both the membrane 28 and the arbor 10.

Turning now to FIG. 2, the applicant's prosthesis is inserted into the medullary cavity 34 of the patient's femur 36. An important feature of the invention is that the arbor 10 and its encompassing membrane 28 and sheath 32 are slim enough that much less chiseling or reaming of the medullary cavity is required than that needed when trying to mechanically fix a prosthesis of established configuration within the cavity. The depth of insertion of the arbor 10 is controlled so that the femoral ball head 14 is properly positioned relative to the acetabular component in the patient's hip. This is accomplished by positioning the collar 18 on the arbor 10 so that the lower face 26 thereof bears against the upper surface of the femur 36 with the proper amount of extension of the arbor.

With the prosthesis in place, the first step is to withdraw all the air from the thin, flexible membrane through the passageway 22. This collapses the membrane 28 inwardly against the arbor. After all the air is withdrawn, liquid cement 40 is then injected through the passageway 22 into the membrane under pressure. The preferred cement is methylmethacrylate which can be injected into the membrane in liquid form and which hardens and sets very quickly. Because the cement is injected into the membrane in liquid form under pressure, the membrane and metallic sheath are forced outwardly against the inner surface of the medullary cavity 34 and form a close, tight fit that conforms to all the irregularities of the medullary cavity.

This very tight fixation of the prosthesis with the femoral bone 38 is shown in FIG. 3. The very small interstices 33 formed in the metallic sheath 32 constitute openings into which the patient's cancellous bone 42 can grow thereby forming an extremely strong fixation between the bone and the sheath 32 of the applicant's prosthesis. Due to the thinness and flexibility of the balloon-like membrane 28 and the force of the liquid cement 40 under pressure, the outer surface of the membrane 28 is forced into the tiny openings 33 in the metallic sheath 32 to form a very tight fixation between the metallic sheath 32, the membrane 28 and the cement 40 once it hardens. At the same time, the interposition of the polyurethane membrane 28 between the cement 40 and the bodily fluids in the patient's bone serves to eliminate any toxicity problems that might otherwise occur.

It is important that the membrane 28 be properly sized so as to allow for the volume of liquid cement injected into the membrane under pressure during the fixation of the prosthesis within the medullary cavity. If the membrane is made from a material that is not elastic, such as polyurethane film, the volume of the membrane must be such as to accept the volume of liquid cement required to fix the prosthesis within the bone without stretching so as to avoid any possibility of accidental rupture of the membrane during the placement of the prosthesis.

The applicant's invention provides a prosthesis, and a method of fixation of that prosthesis within the medullary cavity, that results in a much stronger fixation of the prosthesis in the patient's femoral bone. This result arises from three separate aspects of the invention. There is, first, the high degree of fixation achieved by the outward pressure of the cement which forces the metallic sheath 32 into intimate contact with the irregular contours of the medullary cavity 24. The second aspect is the increased fixation that occurs with the growth of the patient's cancellous bone 42 into the interstices 33 of the metallic sheath 32. This growth serves to anchor the sheath in the medullary cavity with great force. Finally, there is the additional fixation that occurs between the sheath 32, the membrane 28 and the hardened cement 40 which occurs because of the intertwining contact between these elements of applicant's prosthesis in the interstices 33 of the sheath 32.

As previously stated, the invention may be used to fix an orthopedic device in a bone cavity in other parts of the body beside the femur and the adaptation of the invention to the fixation of an orthopedic device in the hip acetabulum of a patient is shown in FIGS. 4-11 as an example of this. In the version shown in FIGS. 4-7 an orthopedic device comprising an acetabular cup 50, and containing a hemispherical recess 52, is provided with one or more grooves 54,54 formed in its outer circumference. A nonresorbable, flexible membrane 56 and a flexible, woven sheath 58 are sealed to the cup 50 in an air and liquid-tight manner and, to this end, the outer edges of the membrane and the sheath are anchored by a lock ring 55 in a circumferential slot 57 formed adjacent the outer face 60 of the cup 50. The sheath 58 comprises a knitted weave of either metal or other suitable bioinert material and this construction imparts a desirable resiliency to it. As seen in the drawings, the acetabular cup 50 is deliberately made smaller than the patient's acetabulum cavity 62 and the flexible membrane 56 and sheath 58 fit in the clearance 64 between the cup and the acetabulum. Duplicate passageways 66,66 are formed in the cup 50 to provide communication between the outer face 60 of the cup and the inside of the flexible membrane 56 whereby fluid cement may be introduced under pressure into the membrane when it is desired to fix the orthopedic device permanently into the acetabular cavity 62.

The fixation of the orthopedic device in the acetabulum is similar to that earlier described with respect to the fixation of the orthopedic device in the femur. As in the earlier instance, the nonresorbable membrane 56 and the woven sheath 58 are secured to the orthopedic device and completely encompass it. With the cup 50 positioned in the acetabular cavity 62, air is first withdrawn from within the flexible membrane through the passageways 66,66. Liquid cement under pressure is then injected into the space enclosed by the membrane and the cement forces the membrane 56 and sheath 58 outwardly against the wall of the acetabular cavity to form a close, tight fit that conforms with all the irregularities of the acetabular cavity. While the cement is hardening, pressure must be applied to the face 60 of the cup 50 to prevent the pressure of the cement from "popping" the cup out of the acetabulum. Although a single passageway 66 is all that is needed in the operation of the invention, it is preferred to utilize passageways 66,66 for the second passageway can then serve as an exhaust vent for any residual air that may be present in the clearance space during the injection of the liquid cement. Utilization of this exhaust vent insures that there will be no air pockets in the cement as it hardens. The circumferential grooves 54,54 formed in the cup provide a grip for the cement because, after the cement has set, they firmly anchor the prosthesis in the acetabular cavity.

Another form of an acetabular prosthesis is shown in FIGS. 8–10. In this form of the invention, the flexible membrane 56 and woven sheath 58 are divided into two separate chambers A and B. As before, the cup 50 is provided with circumferential grooves 54,54 which serve as recesses for the cement. The cup 50 is also provided with two slots 57,57 and a pair of lock rings 55,55 that hold the membrane and sheath in firm contact with the cup to form air and liquid-tight seals between the membrane and the cup. One passageway 65 in the cup communicates the outer face 60 of the cup with the outer chamber A of the membrane and a second passageway 67 communicates the outer face 60 of the cup with the inner chamber B. As is best seen in FIG. 9, liquid cement is first injected into the outer chamber A and allowed to harden. This forces the membrane 56 and sheath 58 of chambaer A into a close, tight fit with the wall of the acetabulum and firmly secures the cup 50 in the cavity without the need to exert an inwardly-directed, external pressure on the cup. As shown in FIG. 10, liquid cement under pressure can then be injected internally of membrane 56 of inner chamber B to force the membrane and sheath of this chamber into a close, tight fit with the patient's acetabulum and thereby complete the fixation of the orthopedic device in the acetabular cavity.

A further modification of this last form of the invention is shown in FIG. 11. This form of the invention employs the two chamber arrangement but the inner chamber B comprises an annular chamber similar to the outer chamber A. Fixation of this form of the invention is the same as that just described for the invention shown in FIGS. 8–10.

I claim:

1. A prosthesis adapted for fixation within the medullary cavity of a human bone, said prosthesis comprising:
   (a) a rigid arbor adapted to fit within the medullary cavity of the bone,
   (b) locating means for selectively positioning the arbor within the medullary cavity,
   (c) a nonresorbable, flexible membrane encompassing said arbor and secured to said locating means in a liquid and air tight manner, said membrane being impervious and inert to human bodily fluids,
   (d) a flexible, woven sheath secured to said locating means and encompassing said arbor and membrane, and
   (e) means for introducing liquid cement under pressure internally of said flexible membrane.

2. A prosthesis adapted for fixation in the medullary cavity of a human bone as set forth in claim 1 wherein said arbor is shaped to generally conform to the shape of the medullary cavity.

3. A prosthesis adapted for fixation in the medullary cavity of a human bone as set forth in claim 2 wherein said locating means comprise a lockable collar selectively positioned on said arbor.

4. A prosthesis adapted for fixation within the medullary cavity of a human bone as set forth in claim 3 wherein said collar has a passageway communicating the periphery of the collar with the interior of the flexible membrane whereby liquid cement under pressure may be introduced into said membrane.

5. A prosthesis adapted for fixation within the medullary cavity of a human bone as set forth in claim 4 wherein said flexible sheath comprises finely woven metallic threads.

6. A prosthesis adapted for fixation within the medullary cavity of a human bone femur bone, said prosthesis comprising:
   (a) a rigid arbor adapted to fit within the proximal end of the medullary cavity of a femur bone, said arbor being generally shaped to conform to the shape of medullary cavity and having a straight section of uniform diameter,
   (b) an annular, lockable collar selectively positioned on said straight section having an inner surface for engagement with the femoral bone so as to position said arbor in the medullary cavity,
   (c) a nonresorbable, flexible membrane encompassing said arbor and secured to the collar in a liquid and air tight manner, said membrane being impervious and inert to human bodily fluids,
   (d) a flexible, metallic woven sheath secured to said collar and encompassing said arbor and flexible membrane,
   (e) means for introducing liquid cement under pressure internally of said flexible membrane.

7. A method of fixing a prosthesis within the medullary cavity of a human bone, said method comprising:
   (a) attaching a nonresorbable, flexible membrane in a liquid and air tight manner to a rigid arbor,
   (b) securing a finely woven, flexible sheath to the arbor so that the sheath encompasses the arbor and the membrane,
   (c) inserting the arbor, membrane and sheath into the medullary cavity,
   (d) filling the flexible membrane with liquid cement under pressure to force the membrane into intimate contact with the sheath and the sheath into intimate contact with the walls of the medullary cavity, and
   (e) allowing the cement to harden while the membrane and the sheath are pressed outwardly against the walls of the medullary cavity.

8. A method of fixing a prosthesis within the medullary cavity of a human bone as set forth in claim 7 wherein said flexible membrane is impervious and inert to human bodily fluids.

9. A method of fixing a prosthesis within the medullary cavity of a human bone as set forth in claim 8 wherein the depth of penetration of the arbor, membrane and sheath into the medullary cavity is selectively controlled according to the size of said cavity.

10. A prosthesis adapted for fixation within the medullary cavity of a human bone, said prosthesis comprising:
    (a) an orthopedic device adapted for insertion into the medullary cavity of a human bone,
    (b) a nonresorbable, flexible membrane secured to said orthopedic device in a liquid and air tight manner, said membrane being impervious and inert to human bodily fluids,
    (c) a flexible woven sheath secured to said orthopedic device and encompassing said membrane, and (d) means for introducing liquid cement under pressure internally of said flexible membrane.

11. A prosthesis adapted for fixation within the medullary cavity of a human bone as set forth in claim 10 wherein said flexible membrane at least partially encompasses said orthopedic device.

12. A prosthesis adapted for fixation within the medullary cavity of a human bone as set forth in claim 11 wherein said orthopedic device has at least one passageway communicating the outer face of the device with the interior of the flexible membrane whereby liquid cement may be introduced internally of said membrane.

13. A prosthesis adapted for fixation within the hip acetabular cavity, said prosthesis comprising:
  (a) an acetabular cup generally shaped to fit within the acetabular cavity,
  (b) a nonresorbable, flexible membrane secured to the acetabular cup in a liquid and air tight manner, said membrane being impervious and inert to human bodily fluids,
  (c) a flexible woven sheath secured to said acetabular cup and encompassing said membrane, and
  (d) means for introducing liquid cement under pressure internally of said membrane.

14. A prosthesis adapted for fixation within the hip acetabular cavity as set forth in claim 13 wherein said acetabular cup has at least one passageway communicating the outer face of said cup with the interior of said membrane.

15. A prosthesis adapted for fixation within the hip acetabular cavity as set forth in claim 14 wherein said membrane and sheath are formed into two separate chambers.

16. A prosthesis adapted for fixation within the hip acetabular cavity as set forth in claim 15 wherein said acetabular cup has passageways communicating the outer face of said cup with each chamber of said membrane.

17. A method of fixing a prosthesis within a human bony cavity, said method comprising:
  (a) attaching a nonresorbable, flexible membrane in a liquid and air tight manner to an orthopedic device,
  (b) securing a finely woven, flexible sheath to the orthopedic device so that the sheath encompasses said membrane,
  (c) inserting the orthopedic device, membrane and sheath into the bony cavity,
  (d) filling the membrane with liquid cement under pressure to force the membrane into intimate contact with the sheath and the sheath into intimate contact with the walls of the bony cavity, and
  (e) allowing the cement to harden while the membrane and the sheath are pressed outwardly against the walls of the bony cavity.

18. A method of fixing a prosthesis within a human bony cavity as set forth in claim 17 wherein said membrane and said sheath are divided into two separate chambers with one chamber disposed adjacent the outer edge of the bony cavity and said one chamber is filled with liquid cement under pressure and the cement is allowed to harden before the other of said chambers is filled with liquid cement.

* * * * *